United States Patent
Clapper

(10) Patent No.: US 6,827,474 B2
(45) Date of Patent: Dec. 7, 2004

(54) FLAME LAMP WITH LIGHT PIPE

(76) Inventor: Edward Owen Clapper, 101 E. Riviera Dr., Tempe, AZ (US) 85282

( * ) Notice: Subject to any disclaimer, the term of this patent is extended or adjusted under 35 U.S.C. 154(b) by 63 days.

(21) Appl. No.: 10/273,284

(22) Filed: Oct. 17, 2002

(65) Prior Publication Data

US 2004/0076017 A1 Apr. 22, 2004

(51) Int. Cl.⁷ .................................................. F21V 5/02
(52) U.S. Cl. ........................ 362/557; 362/159; 362/154; 362/161; 362/335; 362/171; 431/126
(58) Field of Search ............................... 362/557, 159, 362/268, 154, 161, 317, 335, 171; 431/288, 126

(56) References Cited

U.S. PATENT DOCUMENTS

| | | | |
|---|---|---|---|
| 4,134,718 A | * | 1/1979 | Kayfetz et al. ............. 431/125 |
| 4,304,547 A | | 12/1981 | Buzil |
| 6,550,936 B2 | * | 4/2003 | Foley .......................... 362/268 |
| 6,551,099 B1 | * | 4/2003 | Kapinski ..................... 431/288 |
| 6,652,606 B1 | * | 11/2003 | Zimmerman .................. 44/268 |

* cited by examiner

Primary Examiner—Stephen Husar
Assistant Examiner—Anabel Ton
(74) Attorney, Agent, or Firm—Richard Calderwood

(57) ABSTRACT

A candle, lantern, or the like, having one or more light pipes. Reception faces of the light pipes gather light from the flame arena, and emission faces of the light pipes emit the gathered light at another location. The other location may be an exterior surface of the candle, or a decorative fixture. Multiple sets of light pipes may come into play at various times during the life of the candle. The reception faces may move as the candle burns, to stay in the flame arena.

37 Claims, 11 Drawing Sheets

FLAME LAMP WITH LIGHT PIPE

BACKGROUND OF THE INVENTION

1. Technical Field of the Invention

This invention relates generally to candles, and more specifically to candles and lanterns having a light pipe for conducting light from the flame arena to another location.

2. Background Art

Candles and lanterns have been used for thousands of years, to provide reading light, to create a romantic ambiance, to provide aesthetic decoration, and so forth.

Light pipes are a much more modern invention, and are used to conduct light from one location to another. They are used in many applications, such as computers, automobiles, and games. To date, however, they have only been used in conjunction with electric light sources such as incandescent bulbs, lasers, light emitting diodes, and the like. Light pipes can be made using a variety of materials, and can take a variety of forms. One typical form is that of flexible optically conductive fibers commonly known as fiber optic cable.

BRIEF DESCRIPTION OF THE DRAWINGS

The invention will be understood more fully from the detailed description given below and from the accompanying drawings of embodiments of the invention which, however, should not be taken to limit the invention to the specific embodiments described, but are for explanation and understanding only.

DETAILED DESCRIPTION

For simplicity and ease of illustration, the invention will be discussed with reference to candles. It is equally applicable to lanterns and other apparatus which produce light from flame rather than from electricity. Lanterns and candles may, collectively, be termed flame lamps.

Figure 1:
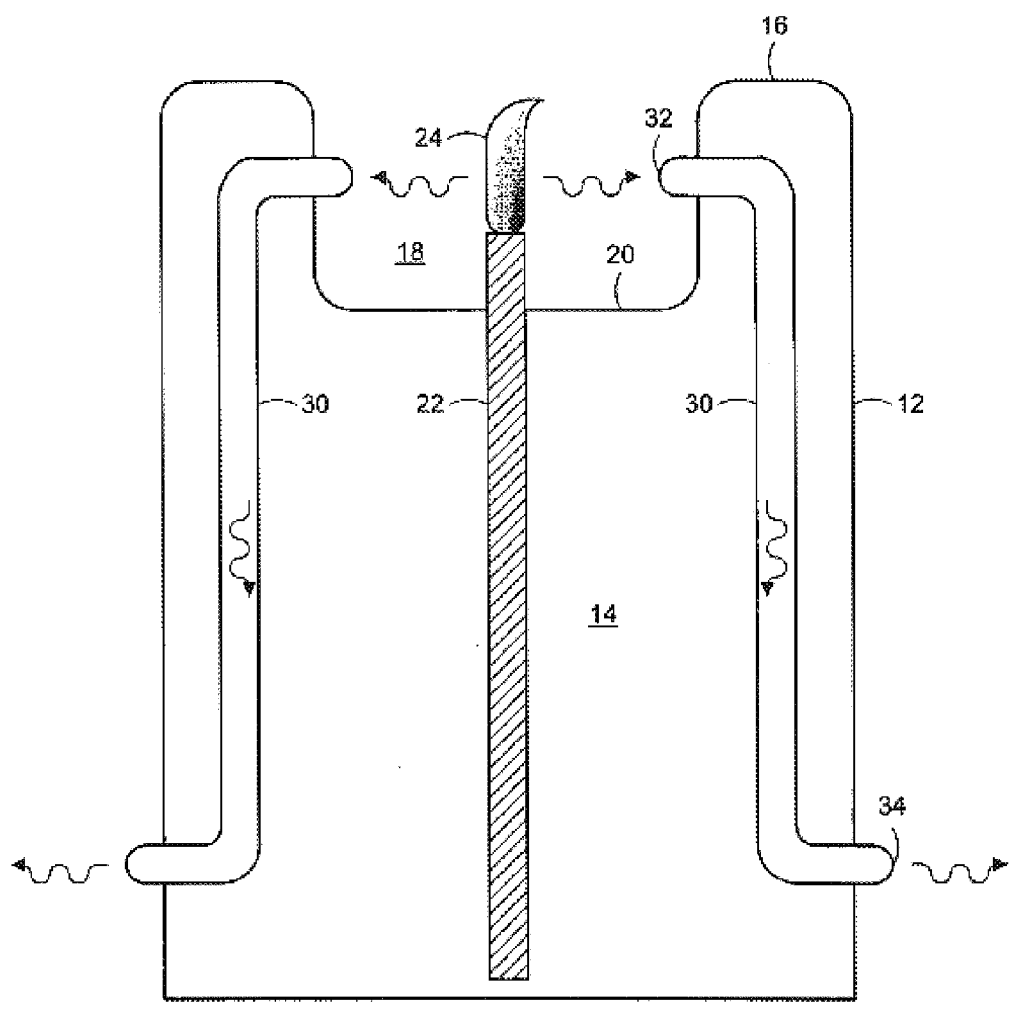
FIG. 1 shows, in cross-section, a light pipe equipped candle according to this invention.

FIG. 1 illustrates one embodiment of a candle 15 according to this invention. The candle includes a combustible body 12 made of any suitable candle material 14 such as wax. Typically, the candle body may optionally include a raised ring portion 16 which surrounds a flame arena 18 which has a floor 20 that is somewhat lower than the ring portion. A wick 22 extends through the body of the candle and into the flame arena. When ignited, the wick draws candle material up into the flame 24. The flame emits heat and also radiation (shown as wavy arrows), some of which is in the visible spectrum, and some of which conducts heat in the infrared spectrum. This heat melts the candle material from the floor and from the raised ring of the candle, slowly flowing them toward the wick. The flame arena is the region around the flame, in which a useable light intensity is present; its boundaries may be rather arbitrarily defined, and its shape and size may change over time, as the candle burns down. The raised ring portion may simply be the rim of the wick recess, if one exists.

The candle further includes one or more light pipes 30. The light pipe has a reception face 32 positioned in the flame arena, and an emission face 34 elsewhere. The reception face receives light from the flame in the flame arena, the light pipe conducts some portion (dictated by the attenuation of the light pipe material and configuration) of that light, and the emission face emits the conducted light.

The skilled reader will appreciate that the light pipes can be formed in a wide variety of shapes and configurations and numbers. It is for ease of illustration only, that only two light pipes are shown in FIG. 1.

Figure 2:
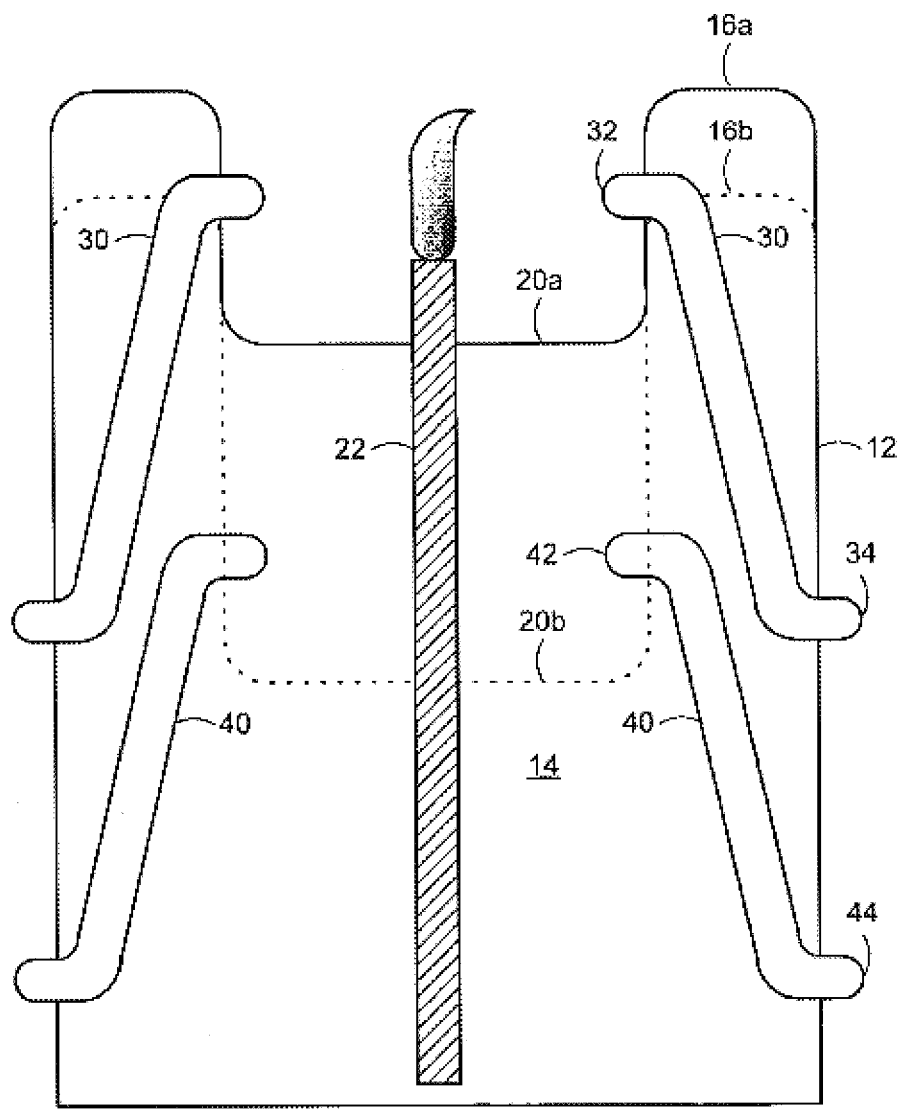
FIG. 2 shows, in cross-section, another embodiment of the invention, in which light pipes are embedded at different locations so their reception faces come into play at different points of the candle's burn life.

FIG. 2 illustrates another embodiment of a candle 25 according to this invention. The body 12 of the candle is made of a combustible material 14. As the material is used up, the candle burns down and the floor falls (from 20a to 20b). This embodiment of the candle includes a first set of one or more light pipes 30 positioned in the candle body to have their reception faces 32 in the flame arena during the early life of the candle, and a second set of one or more light pipes 40 positioned in the candle body to have their reception faces 42 in the flame arena during the later life of the candle. During the early life of the candle, the first set of light pipes 30 will emit light from their emission faces 34. During the later stages of the candle's life, the second set of light pipes 40 will emit light from their emission faces 44. By staging the light pipes in this manner, the pattern of emission face illumination can be significantly changed over the course of the candle's life, with pleasing aesthetic effects, and with improved light pipe emission during the later stages versus what would otherwise be achieved if the flame were to burn down well below the level of the reception faces of a single set of light pipes.

Again, the skilled reader will appreciate that the simplistic pattern of sets of light pipes shown in FIG. 2 is for ease of illustration only.

Figure 3:
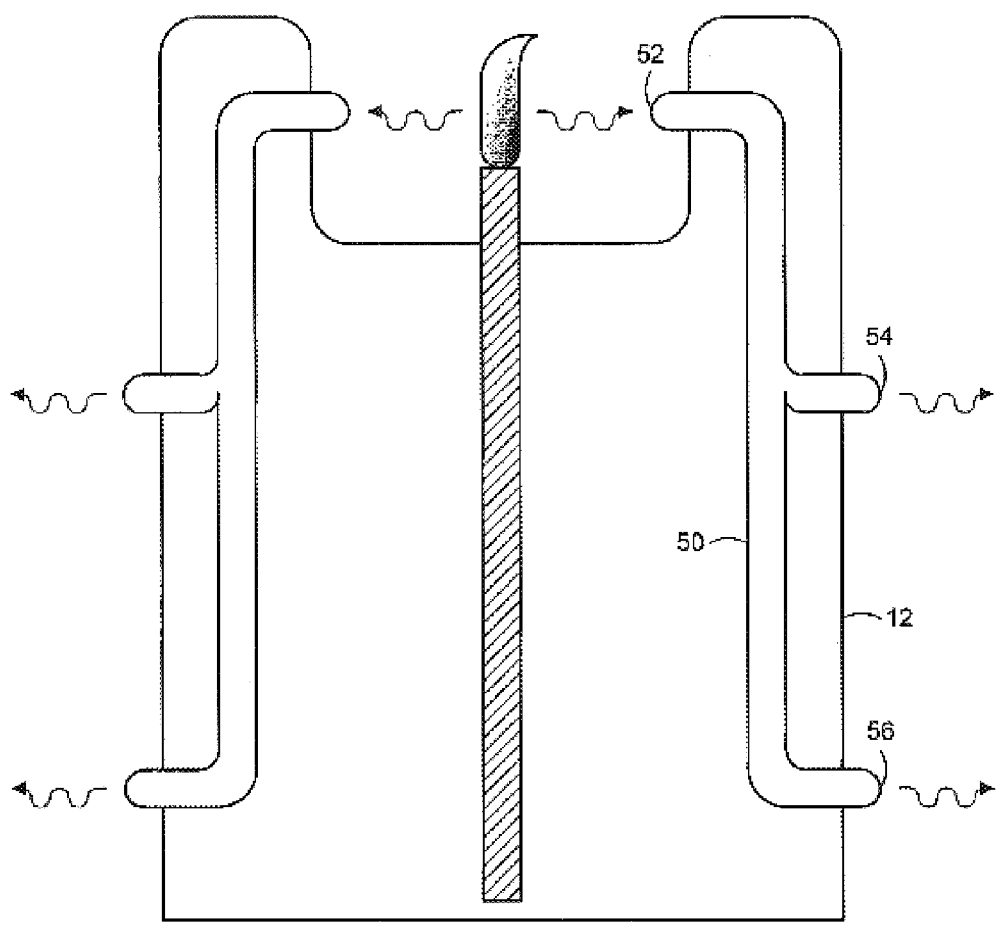
FIG. 3 shows, in cross-section, another embodiment of the invention, in which the light pipes have branched, multiple emission faces.

FIG. 3 illustrates another embodiment of a candle 35, in which one or more light pipes 50 are embedded in the body 12 of the candle. The light pipe is configured such that it has a single reception face 52 which gathers light which is then split up and branched to two or more emission faces 54, 56.

Figure 4:
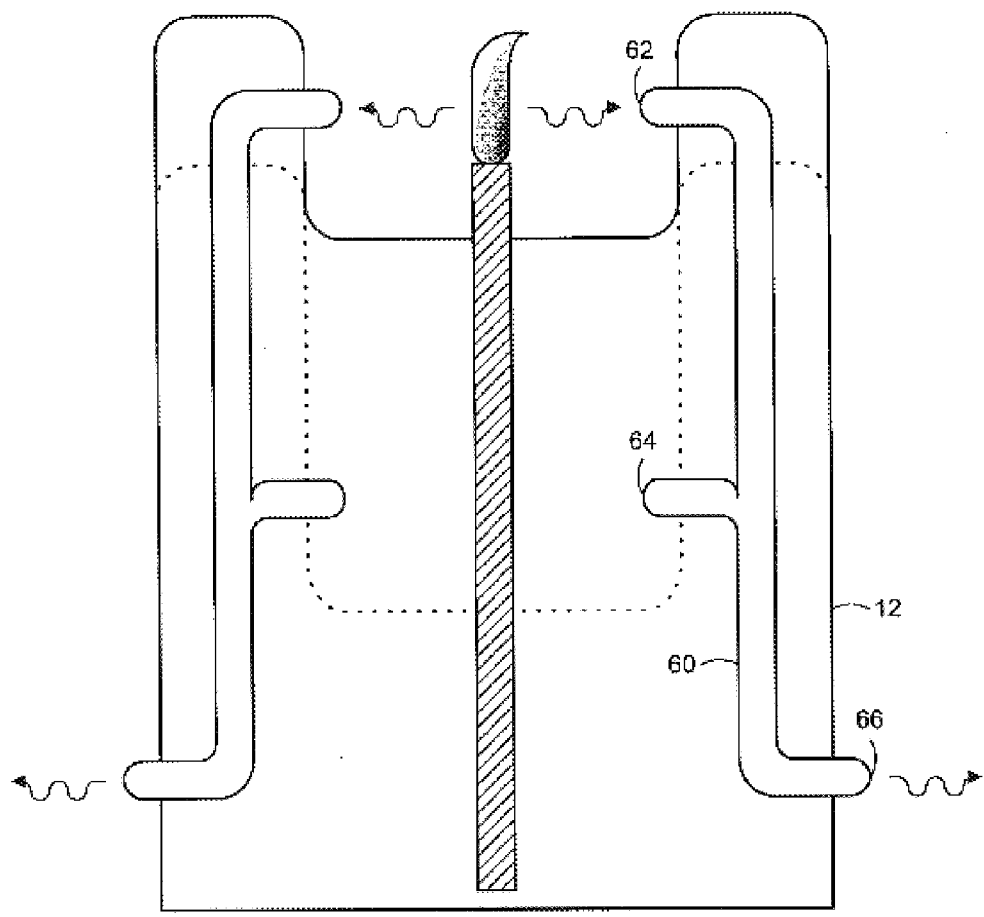
FIG. 4 shows, in cross-section, another embodiment of the invention, in which the light pipes have branched, multiple reception faces.

FIG. 4 illustrates another embodiment of a candle 45, in which one or more light pipes 60 are embedded in the body 12 of the candle. The light pipe is branched such that it has two or more reception faces 62, 64 which branch together to feed a common emission face 66. The reception faces are positioned to gather light at different stages of the candle's life, as the flame arena progresses toward the bottom of the candle.

Figure 5:
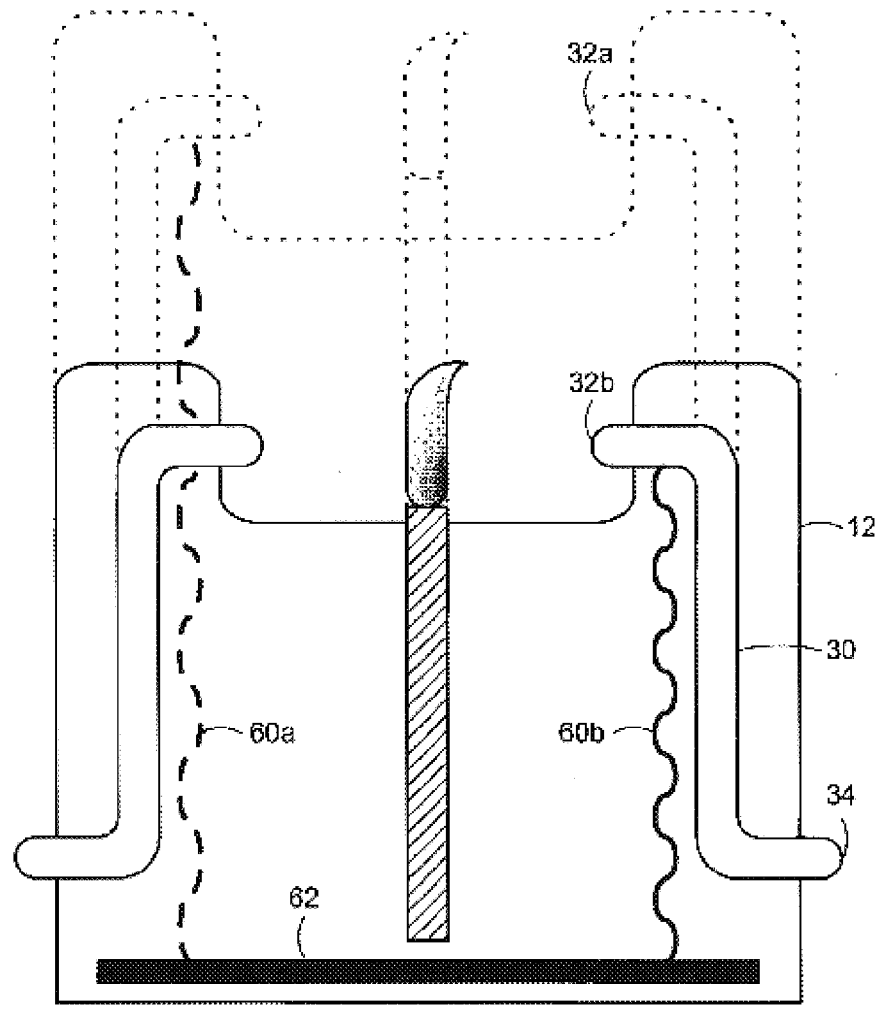
FIG. 5 shows, in cross-section, another embodiment of the invention, in which a retraction mechanism keeps the light pipe' emission faces in the flame arena.

FIG. 5 illustrates another embodiment of a candle 55, in which a tracking mechanism keeps the light pipe's reception face in the flame arena as the candle burns down. In the example shown, a shape memory alloy structure 60 (such as a nitinol wire) is attached between a base 62 and the light pipe 30 near the reception face 32. When the candle is new, the wire is stretched into a long configuration 60a. As the candle burns down, the wire contracts into a shorter configuration 60b, pulling the reception face down (from 32a to 32b) with the flame arena. In some embodiments, a simple spring may be used as the tracking mechanism; the candle is manufactured with the spring under tension, and, as the candle burns, the spring contracts toward its resting configuration, with the unmelted portion of the candle body resisting the spring, keeping the reception face in the flame arena.

As illustrated in FIG. 5, the tracking mechanism can be used in conjunction with a flexible light pipe which is held in position in an elongated configuration when the candle is new, and flexes as the candle burns.

Figure 6:
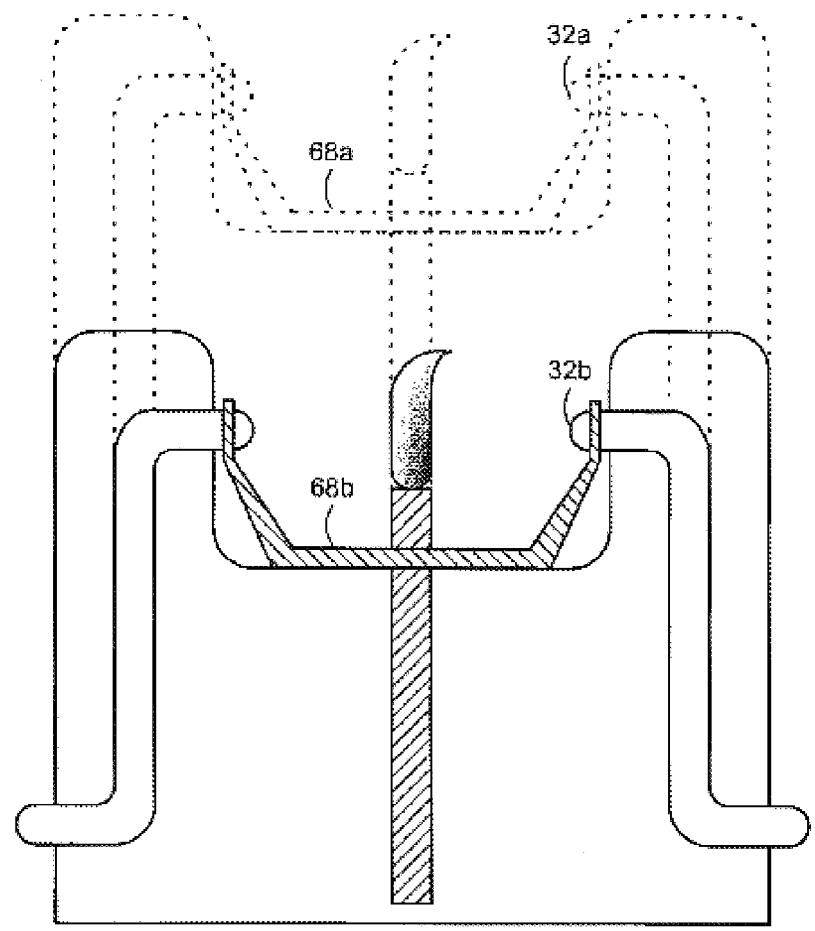
FIG. 6 shows, in cross-section, another embodiment of the invention, with a different retraction mechanism.

FIG. 6 illustrates another embodiment of a candle 65, in which a simpler tracking mechanism 68 keeps the reception face 32 in the flame arena. The tracking mechanism may be a simple fixture 68 connected to the light pipe near the reception face, and resting on the floor of the flame arena. As the candle burns, the floor drops, and gravity pulls the fixture (from 68a to 68b) down with the floor. The fixture, in turn, pulls the reception face (from 32a to 32b) down with the descending flame arena.

Figure 7:
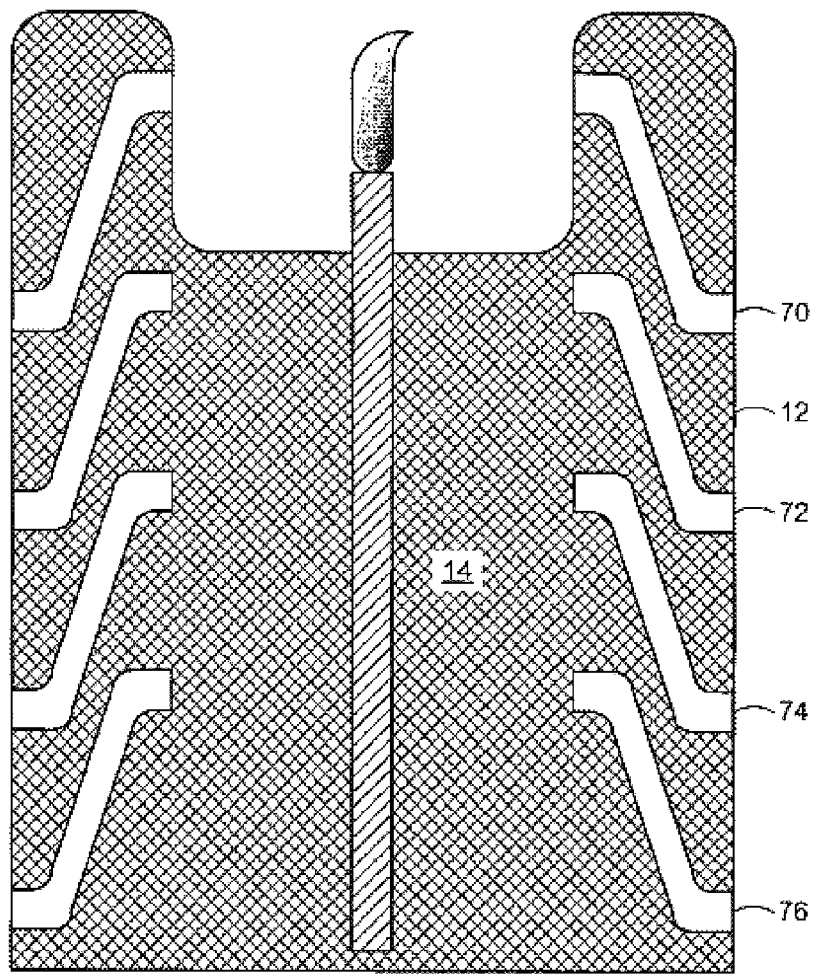
FIG. 7 shows, in cross-section, another embodiment of the invention, in which the light pipes are formed as part of the combustion material of the candle.

FIG. 7 illustrates another embodiment of a candle 75 in which one or more light pipes 70, 72, 74, 76 are formed as meltable, combustible portions of the candle body 12. The light pipes may, for example, be rods of colorless, clear wax gel honeycombed within the regular material 14 of the candle body. As the candle burns down, each successive wax gel light pipe will come into play, with its reception face facing the flame front and conducting light to its emission face which is located somewhere remote from the reception face (as distinguished from known "wax window" candles in which a series of holes come into play as the candle burns, but which merely transmit the light directly out from the flame front). As the raised ring portion of the candle melts down and collapses, the wax gel light pipe will melt with it, eventually being wicked to the flame and burned.

In some embodiments, non-combustible materials may be used for the light pipes, such as water, so long as the light pipes are configured such that their material escapes and does not extinguish the flame. Other materials, such as glycerin, may also be used.

Figure 8:
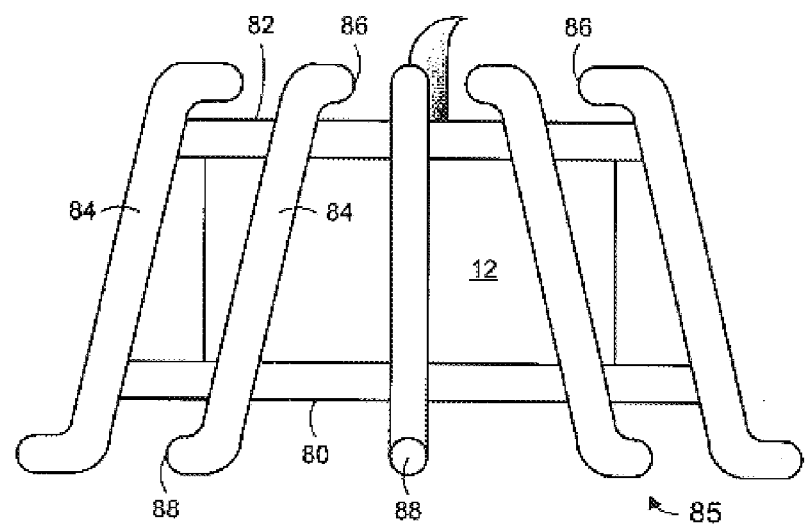
FIG. 8 shows, in front view, another embodiment of the invention, in which the light pipes are external to the combustion material of the candle.

FIG. 8 illustrates an embodiment of a candle 85 in which one or more light pipes are completely external to the body 12 of the candle. In some such embodiments, the light pipes may comprise a candle holder with which a series of replaceable candle bodies 12 may be used. In one such embodiment, the light pipes may comprise legs of the candle holder, held together by one or more support structures 80, 82.

Figure 9:
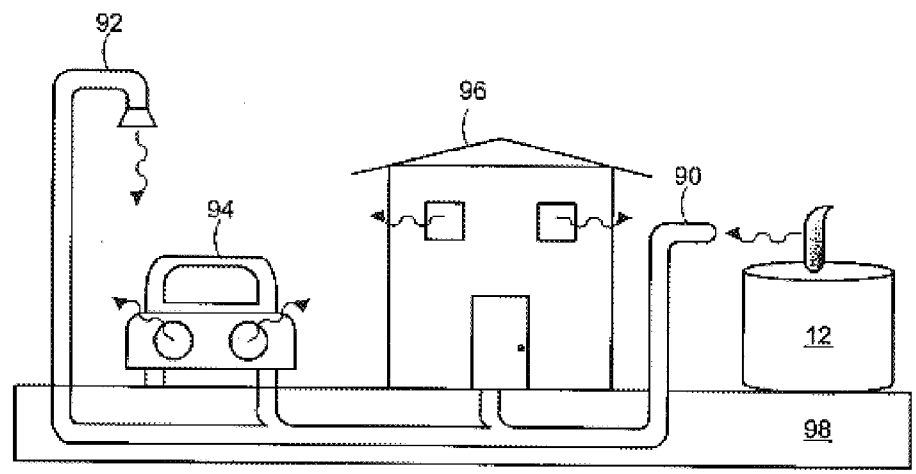
FIG. 9 shows, in front view, another embodiment of the invention, in which the light pipe' emission faces are utilized in a decorative scene of the candle.

FIG. 9 illustrates another embodiment of a candle 95 in which one or more candle bodies 12 provide light to one or more light pipes 90, each of which feeds light from the candle(s) to one or more decorative elements or fixtures 92, 94, 96 which may be attached to a base 98. In some embodiments, the light pipes may be routed through the base, as shown. In some embodiments, the candle bodies may be replaceable, and the decorative light fixtures, base, and light pipes may comprise a decorative candle holder, such as a nativity scene or the like. Examples of decorative elements which may include the emission face of a light pipe may include, for example, an automobile headlight, a street lamp, a house window, stars, eyes, and so forth.

Figure 10:
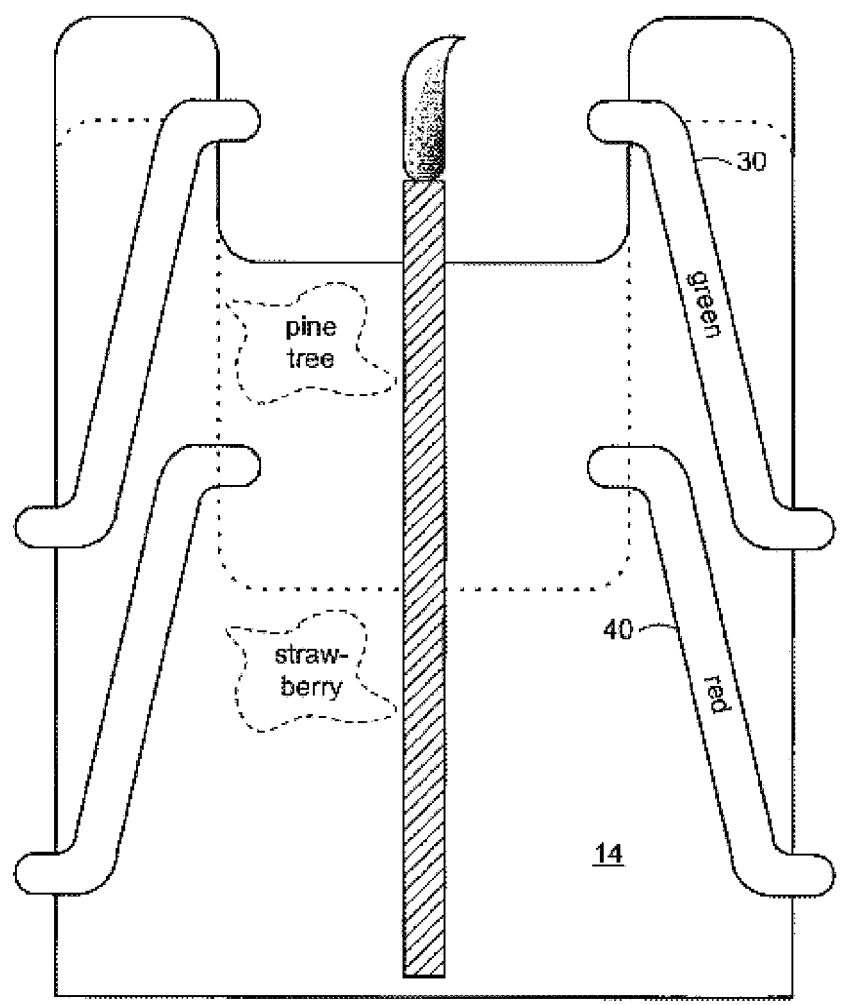
FIG. 10 shows, in cross-section, another embodiment of the invention, in which the candle includes scent which is positioned to be emitted in coordination with illumination of the light pipes.

FIG. 10 illustrates an embodiment of a scented candle 105. In some instances, scents may be added to the candle material. This can be most advantageous in those embodiments in which the pattern of emission faces changes as the candle burns; in these embodiments, different scents may be positioned at different locations in the candle body, to be emitted in synchronism with a respective light emission pattern. For example, during the early life of a candle, a set of green light pipes can be illuminated in conjunction with the emission of the scent of green pine trees, while, later in the candle's life, a set of red light pipes can be illuminated in conjunction with the emission of the scent of red strawberries.

Figure 11:
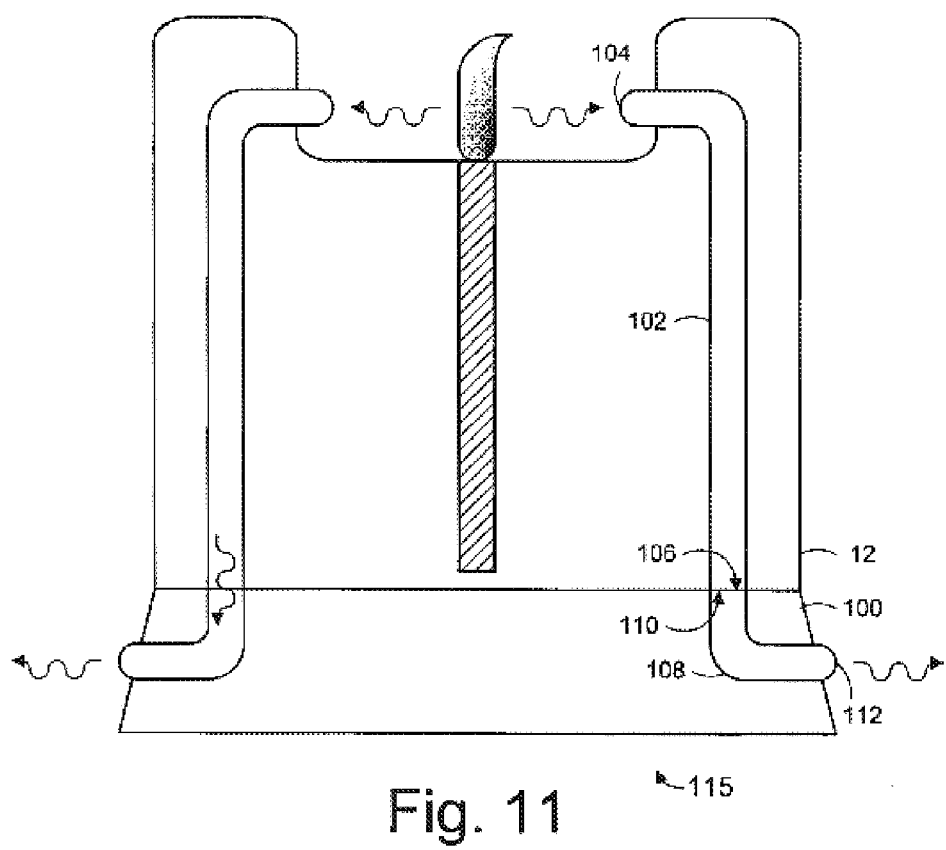
FIG. 11 shows, in cross-section, an embodiment of the invention, in which both the candle and its stand are equipped with light pipes.

FIG. 11 illustrates an embodiment of a candle 115 which includes a candle body 12 and a base 100 or candlestick, both of which are equipped with light pipes. The candle body includes one or more light pipes 102 having a reception face 104 in the flame arena and an emission face 106 which faces toward the candle base. The candle base includes one or more light pipes 108 having a reception face 110 facing the candle body and an emission face 112 which extends out of the base. The emission face 106 of the candle body's light pipe is aligned with the reception face 110 of the base's light pipe, and light is conducted from the flame arena out the final emission face 112. In some embodiments, the candle can be rotated within the candle base, to place the respective light pipes into or out of alignment, in effect turning the light pipes on or off. In some embodiments, the candle body and/or the candle base may include two or more sets of light pipes having differently positioned faces 106, 110, such that by rotating the candle different amounts, different sets of candle base light pipes may be turned on. In some such embodiments, the candle could even be motorized to rotate continuously, causing a winking effect at the one or more sets of candle base light pipe emission faces. A small electric motor could be built into the base. In other embodiments, other rotating mechanisms could be employed, such as spring-driven wind-up mechanisms or the like. As such, the term "motor" is not necessarily intended to be limited to electric motors.

Figure 12:
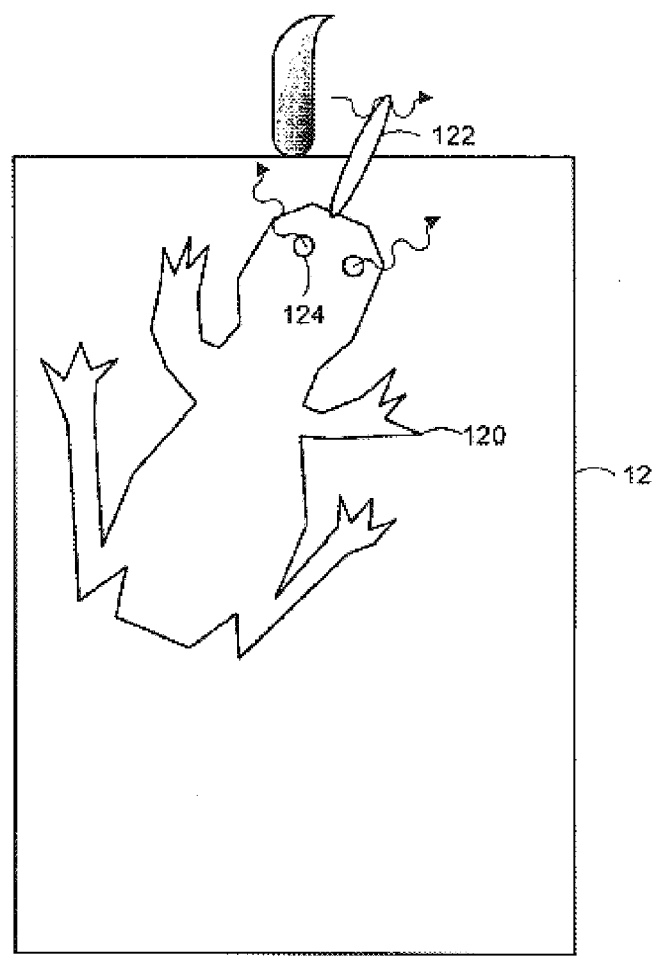
FIG. 12 shows, in side view, another embodiment of the invention, in which the light pipe is external to the candle and comprises a decorative element.

FIG. 12 illustrates another embodiment of a candle 125 in which the light pipe structures are external to the candle body 12. The light pipe structure includes a decorative body 120 which may depict any variety of aesthetic features, such as a frog clinging to the side of the candle. The decorative body includes a light pipe 122 having a reception face which can be positioned in the flame arena, and an emission face 124 which comprises an element of the decorative body, such as the eye of the frog. In the instance shown, the light pipe is branched such that a single reception face at the end of the frog's tongue feeds light to two output faces, one comprising each of the frog's two eyes. The decorative body may further include means (not shown) for holding it to the candle body, such as prongs that can be pressed into the candle wax, or a chain which can be looped around the candle body, or a hanger which hangs from the top surface of the candle; this latter case can provide the advantage of lowering the decorative body as the candle burns down.

The various features illustrated in the various FIGS. may be combined in many ways, and should not be interpreted as though limited to the specific embodiments in which they were explained and shown.

The skilled reader will appreciate that a light pipe could be branched with both "fan-in" and "fan-out", to include both multiple reception faces and multiple emission faces.

Although the reception and emission faces are shown as having a hemispherical shape, other shapes are also useable. In some applications, it may be desirable to form a face as a flat surface. In others, it may be desirable to shape the face with multiple facets or other prismatic forms. In some applications, it may be desirable to have a highly polished, shiny face, while in others it may be desirable to give the face a frosted or otherwise textured face.

The light pipe may be formed of any suitable material, such as glass, plastic, acrylic, polycarbonate, or the like. In some applications, it may be necessary to take into account the melting point when selecting the light pipe material, especially those in which the reception face will be in close proximity to the flame. In some applications, it may be necessary to take other factors into account, such as resistance to sooting. The material should have a suitably high index of refraction, to provide good conduction of the light. The material should have a suitably low attenuation. The material may be colorless, or it may be colored.

The light pipe may be formed with any suitable cross-section or combination of cross-sectional shapes. The emission faces may be positioned in a variety of manners. One suitable configuration will be in a cylindrical pattern around the wick. The candle may include more than one wick; the emission faces may be patterned accordingly.

The reception faces may be directly in the flame arena, separated from the flame only by the ambient air. Or, alternatively, they may be insulated from the flame by an optically conductive barrier, such as glass or gel wax. In some such cases, this barrier may advantageously be thermally insulative.

The emission faces may extend out of the candle body into the ambient air. Or, alternatively, they may be positioned just below the surface of the candle body.

The overall length of the light pipe may be shaped in any suitable configuration, within bounds set by the angle of incidence and index of refraction characteristics of the material. In some embodiments, it may be desirable to frost or texture or notch some portion of the length, causing, in effect, an intermediate emission face. In some embodiments, the length of the light pipe may be coated with a reflective and/or opaque finish, to improve light conductivity and reduce leakage.

In some embodiments, the flame arena may simply be the area around the wick, and the candle body does not include a raised ring of combustible material.

In some embodiments, the candle body is made of a solid combustible material such as paraffin wax. In other embodiments, the candle body is made of a liquid combustible material such as kerosene, and a containment vessel. In still other embodiments, the candle body is made of a gaseous combustible material and a containment vessel; in some such embodiments, the combustible material such as propane may be in a liquid phase under pressure in the containment vessel but convert to gaseous phase before burning; in others, the combustible material such as natural gas is stored or delivered in a gaseous phase. In some embodiments, the wick may comprise a nozzle or jet, rather than a length of wicking material. In some embodiments, the candle may be configured as a lantern or lamp which produces light by burning combustible material.

The various components shown in the FIGS. are not necessarily shown to scale. Sizing the various components is well within the abilities of an ordinary skilled designer, when armed with the teachings of this disclosure.

Reference in the specification to "an embodiment," "one embodiment," "some embodiments," or "other embodiments" means that a particular feature, structure, or characteristic described in connection with the embodiments is included in at least some embodiments, but not necessarily all embodiments, of the invention. The various appearances "an embodiment," "one embodiment," or "some embodiments" are not necessarily all referring to the same embodiments.

If the specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

Those skilled in the art having the benefit of this disclosure will appreciate that many other variations from the foregoing description and drawings may be made within the scope of the present invention. Indeed, the invention is not limited to the details described above. Rather, it is the following claims including any amendments thereto that define the scope of the invention.

What is claimed is:

1. A flame lamp comprising:
   a body including a combustible material;
   a wick disposed within the body in contact with the combustible material; and
   at least one first light pipe including,
      a reception face disposed within a flame arena around the wick,
      an elongated body, and
      an emission face disposed to direct light received by the reception face and conducted by the light pipe away from the flame lamp toward an onlooker.

2. The flame lamp of claim 1 wherein:
   the first light pipe is disposed within the body of the flame lamp.

3. The flame lamp of claim 1 further comprising:
   at least one second light pipe including a reception face disposed within the body in a position such that it will be within the flame arena only after the combustible material has at least partly burned.

4. The flame lamp of claim 1 wherein:
   the first light pipe further including a branched body and a second face which comprises one of a reception face and an emission face.

5. The flame lamp of claim 4 wherein:
   the second face comprises a reception face disposed within the body in a position such that it will be within the flame arena only after the combustible material has at least partly burned.

6. The flame lamp of claim 1 further comprising:
a tracking mechanism which keeps the reception face in the flame arena as the combustible material burns down.

7. The flame lamp of claim 6 wherein the tracking mechanism comprises:
a base; and
one of a shape memory alloy structure and a spring coupled between the base and the light pipe.

8. The flame lamp of claim 6 wherein the tracking mechanism comprises:
a fixture which is coupled to the light pipe, and which is drawn to the body by gravity.

9. The flame lamp of claim 1 wherein the first light pipe comprises:
an elongated body of meltable, combustible, light-conducting material formed within the body of the flame lamp.

10. The flame lamp of claim 9 wherein the meltable, combustible, light-conducting material comprises:
gel wax.

11. The flame lamp of claim 9 further comprising:
at least one second elongated body of meltable, combustible, light-conducting material including a reception face disposed within the body in a position such that it will be within the flame arena only after the combustible material has at least partly burned.

12. The flame lamp of claim 1 wherein:
the first light pipe is entirely external to the flame lamp body.

13. The flame lamp of claim 12 wherein:
the at least one first light pipe includes a plurality of first light pipes which, together, comprise a candle holder.

14. The flame lamp of claim 13 wherein:
the plurality of first light pipes comprise legs of the candle holder.

15. The flame lamp of claim 1 further comprising:
a base to which the body is coupled; and
a decorative fixture coupled to the base;
wherein the emission face of the first light pipe is disposed within the decorative fixture.

16. The flame lamp of claim 15 wherein:
the decorative fixture includes an element which models a real world object which emits light; and
the emission face is disposed at that element.

17. The flame lamp of claim 1 further comprising:
a first scent disposed within the body;
a second scent disposed within the body; and
at least one second light pipe including a reception face disposed within the body in a position such that it will be within the flame arena when the combustible material has at least partly burned;
wherein the first scent is disposed in a location such that it will be emitted in conjunction with illumination of the first light pipe, and the second scent is disposed in a different location such that it will be emitted later in conjunction with illumination of the second light pipe.

18. The flame lamp of claim 1 further comprising:
a base holding the body; and
the first light pipe comprising a first light pipe segment which includes the reception face and a second light pipe segment which includes the emission face, wherein the second light pipe segment includes a reception face which is alignable with an emission face of the first light pipe segment.

19. The flame lamp of claim 18 wherein:
the body is rotatable within the base to align and unalign the emission face of the first light pipe segment with the reception face of the second light pipe segment.

20. The flame lamp of claim 1 wherein the light pipe comprises:
a decorative structure coupled to an exterior surface of the body.

21. The flame lamp of claim 1 wherein the combustible material is in a solid phase and the flame lamp comprises a candle.

22. The flame lamp of claim 1 wherein the combustible material is in a liquid phase and the flame lamp comprises a lantern.

23. The flame lamp of claim 1 wherein the combustible material is in a gaseous phase and the flame lamp comprises a lantern.

24. A method of operating a flame lamp which contains combustible material, the method comprising:
burning the combustible material with a flame in a flame arena;
collecting light from the flame at a reception face of an elongated light pipe disposed within the flame arena;
conducting collected light through the light pipe; and
emitting conducted light at an emission face of the light pipe for viewing by an onlooker.

25. The method of claim 24 further comprising:
as the combustible material burns down, automatically moving the reception face of the light pipe by a tracking mechanism coupled to the light pipe.

26. The method of claim 24 further comprising:
as the combustible material burns down, exposing a reception face of another light pipe to the flame; and
emitting light from an emission face of the other light pipe.

27. The method of claim 26 further comprising:
emitting a first scent in conjunction with the emitting of light from the first light pipe; and
as the combustible material burns down, emitting a different second scent in conjunction with the emitting of light from the second light pipe.

28. The method of claim 24 wherein the light pipe includes a first light pipe segment having the reception face and a second light pipe segment having the emission face, and wherein the second light pipe segment is disposed within a base to which the flame lamp is coupled, the method further comprising:
receiving light from the emission face of the first light pipe segment at the reception face of the second light pipe segment.

29. The method of claim 28 further comprising:
rotating the flame lamp on the base, by means of a motor, to align and unalign the first and second light segments.

30. A candle comprising:
a combustible wax body;
a wick disposed within the combustible wax body; and
a light pipe including,
an elongated light pipe body disposed within the combustible wax body,
a reception face disposed within a flame arena around the wick, and
an emission face protruding through an exterior surface of the combustible wax body toward an onlooker.

31. The flame lamp of claim 1 wherein the elongated body of the light pipe comprises:

glass.

32. The flame lamp of claim 1 wherein the elongated body of the light pipe comprises:

acrylic.

33. The flame lamp of claim 1 further comprising:

a lumulet body removably coupled to the candle; and the at least one light pipe being coupled to the lumulet body.

34. The flame lamp of claim 33 further wherein:

the at least one light pipe coupled to the lumulet body comprises a plurality of light pipes, wherein the reception faces of the plurality of light pipes are grouped substantially together and the emission faces of the plurality of light pipes are distributed about the lumulet body.

35. The flame lamp of claim 1 further comprising:

a base;

a plurality of decorative elements coupled to the base;

the body comprising a candle disposed upon the base;

the elongated body of the light pipe extending from the flame arena to one of the decorative elements; and the emission face disposed to emit from the one of the decorative elements light received by the reception face and conducted by the elongated body.

36. The flame lamp of claim 9 wherein the meltable, combustible, light-conducting material comprises:

clear wax.

37. A candle comprising:

a combustible wax body;

a wick disposed within the combustible wax body; and an elongated light pipe disposed within the combustible wax body and having a reception face aligned to receive light from a flame at the wick, and an emission face aligned to direct the received light away from the combustible wax body.

* * * * *